United States Patent [19]
Shawver et al.

[11] Patent Number: 5,695,849
[45] Date of Patent: Dec. 9, 1997

[54] ELASTIC, BREATHABLE, BARRIER FABRIC

[75] Inventors: Susan Elaine Shawver; Leslie Warren Collier, IV, both of Roswell; Paul Windsor Estey, Cumming; Susan Carol Paul, Alpharetta, all of Ga.

[73] Assignee: Kimberly-Clark Worldwide Inc., Irving, Tex.

[21] Appl. No.: 602,548

[22] Filed: Feb. 20, 1996

[51] Int. Cl.$^6$ .................... A61F 13/66; B32B 5/04
[52] U.S. Cl. .................... 428/131; 428/137; 428/152; 428/195; 428/219; 428/311.51; 428/315.9; 442/118; 442/329; 604/385.1
[58] Field of Search .................... 428/131, 137, 428/152, 195, 219, 311.51, 315.9; 442/118, 329; 604/385.1

[56] References Cited

U.S. PATENT DOCUMENTS

| | | | |
|---|---|---|---|
| 3,338,992 | 8/1967 | Kinney | 264/24 |
| 3,341,394 | 9/1967 | Kinney | |
| 3,502,538 | 3/1970 | Peterson | |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | |
| 3,855,046 | 12/1974 | Hansen et al. | |
| 4,041,203 | 8/1977 | Brock et al. | 428/157 |
| 4,340,563 | 7/1982 | Appel et al. | 264/518 |
| 4,374,888 | 2/1983 | Bornslaeger | 428/198 |
| 4,542,199 | 9/1985 | Kaminsky et al. | 526/160 |
| 4,631,933 | 12/1986 | Carey, Jr. | 66/192 |
| 4,652,487 | 3/1987 | Morman | 428/138 |
| 4,655,760 | 4/1987 | Morman et al. | 604/385 |
| 4,657,802 | 4/1987 | Morman | 428/152 |
| 4,663,220 | 5/1987 | Wisneski et al. | 428/221 |
| 4,692,368 | 9/1987 | Taylor et al. | 428/137 |
| 4,692,371 | 9/1987 | Morman et al. | 428/224 |
| 4,704,116 | 11/1987 | Enloe | 604/385 |
| 4,710,187 | 12/1987 | Boland et al. | 604/385 |
| 4,720,415 | 1/1988 | Vander Wielen et al. | 428/152 |
| 4,781,966 | 11/1988 | Taylor | 428/152 |
| 4,789,699 | 12/1988 | Kieffer et al. | 524/271 |
| 4,822,435 | 4/1989 | Igaue et al. | 156/164 |
| 4,965,122 | 10/1990 | Morman | 428/225 |
| 4,981,747 | 1/1991 | Morman | 428/198 |
| 5,026,364 | 6/1991 | Robertson | 604/385.1 |
| 5,064,802 | 11/1991 | Stevens et al. | 502/155 |
| 5,108,820 | 4/1992 | Kaneko et al. | 428/198 |
| 5,108,827 | 4/1992 | Gessner | 428/219 |
| 5,169,706 | 12/1992 | Collier, IV et al. | 428/152 |
| 5,189,192 | 2/1993 | LaPointe et al. | 556/11 |
| 5,204,429 | 4/1993 | Kaminsky et al. | 526/308 |
| 5,226,992 | 7/1993 | Morman | 156/62.4 |
| 5,272,236 | 12/1993 | Lai et al. | 526/348.5 |
| 5,278,272 | 1/1994 | Lai et al. | 526/348.5 |
| 5,304,599 | 4/1994 | Himes | 525/98 |
| 5,336,545 | 8/1994 | Morman | 428/152 |
| 5,336,552 | 8/1994 | Strack et al. | 428/224 |
| 5,349,100 | 9/1994 | Mintz | 585/350 |
| 5,352,749 | 10/1994 | DeChellis et al. | 526/68 |
| 5,374,696 | 12/1994 | Rosen et al. | 526/126 |
| 5,376,198 | 12/1994 | Fahrenkrug et al. | 156/164 |
| 5,382,400 | 1/1995 | Pike et al. | 264/168 |
| 5,413,570 | 5/1995 | Enloe | 604/385.2 |
| 5,415,644 | 5/1995 | Enloe | 604/385.2 |

FOREIGN PATENT DOCUMENTS

| | | | |
|---|---|---|---|
| 0 602 613 A | 6/1994 | European Pat. Off. | D04H 1/56 |
| 0 712 892 | 5/1996 | European Pat. Off. | C08L 23/16 |

OTHER PUBLICATIONS

G. W. Coates, et al. "*Oscillating Stereo Control: A Strategy For The Synthesis Of* Thermoplastic Elastomeric Polypropylene", P. 217.
K. B. Wagner, Science, vol. 267, Jan. 13, 1995, p. 191.
John Manson, et al. *Polymer Blends & Composites*, Plenum Press, Plenum Publication. pp. 273–277.
C. Allen Bodford, et al. *Multidenier NW Fabrics For Leg Cuff And Other Diaper* Applications, Nonwovens World, Summer 1995 pp. 59–62.

*Primary Examiner*—James C. Cannon
*Attorney, Agent, or Firm*—James B. Robinson

[57] ABSTRACT

There is provided a fully elastic, breathable, barrier fabric comprising a nonwoven web layer of fibers, where the web has a hydrohead of at least 4 mbar, a basis weight of less than 68 gsm and which is made from an elastic polyolefin. If the fabric is a laminate it may be an SMS, SBL or NBL laminate. This fabric is particularly well suited to use as a containment flap for personal care products such as diapers, incontinence products and feminine hygiene products and in infection control products. The fabric may also be used as a liner in personal care products.

12 Claims, No Drawings ately well suited use for the disclosed invention.

ELASTIC, BREATHABLE, BARRIER FABRIC

BACKGROUND OF THE INVENTION

This invention relates to nonwoven fabrics for use in various personal care products such as diapers, training pants, adult incontinence products, feminine hygiene products and any other type of article used to contain bodily fluids. More particularly, personal care products generally include containment flaps which serve to keep the managed fluids from escaping from the article and soiling the clothing or bedding of the wearer. Personal care products also usually include liners which go against the skin of the wearer and serve to move liquids away from the skin to the absorbent layers of the product. These containment flaps and liners are an especially well suited use for the disclosed invention.

In order for such containment articles to function efficiently, the fabric must have sufficient barrier properties to perform its primary function of containing fluids, yet must also be breathable so as not to inhibit skin comfort. The fabric should ideally be elastic to conform to the body of the wearer and recover from stretching due to the movement of the wearer, all the while continuing to perform its function as a barrier. In the past, containment flaps have been made with separate materials supplying the various functions desired. Elastic threads, for example, have been joined with non-elastic materials to supply the requisite elasticity. While these attempts to solve the problem of breathability with barrier properties for an elastic member have been partially successful, there remains a need for a single material which will have the needed barrier and breathability and which is elastic. It is further preferred that the material have these properties without the addition of any topical treatments.

When functioning as a liner, the fabric must feel comfortable against the skin and must also quickly pass any liquids through to the next, absorbent layer(s). Since the fabric is a barrier fabric, it is desirable that the fabric be treated to increase its wettability or have natural hydrophilicity when functioning as a liner. Such topical treatments like wetting agents are known in the art.

It is an object of this invention to provide a unitary, fully elastic, breathable, barrier nonwoven fabric which may be used in personal care products and which will be a comfortable and effective means of containing fluids within the article. It is a further object of this invention to provide a liner material which will pass liquids through itself rapidly. It is a further object of this invention to provide a unitary liner and containment flap material.

SUMMARY OF THE INVENTION

The objects of the invention are satisfied by a elastic, breathable, barrier fabric comprising a web of nonwoven fibers where the web has a hydrohead of at least 4 mbar, and which is elastic. This fabric is particularly well suited to use as a containment flap and/or liner for personal care products such as diapers, incontinence products and feminine hygiene products.

DEFINITIONS

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2$=0.89×0.00707=1.415). Outside the United States the unit of measurement is more commonly the "tex", which is defined as the grams per kilometer of fiber and which may be calculated as denier/9.

As used herein the term "composite elastic material" refers to an elastic material which may be a multicomponent material or a multilayer material in which one layer is elastic. These materials may be, for example, "stretch bonded" laminates (SBL) and "neck bonded" laminates (NBL).

Conventionally, "stretch bonded" refers to an elastic member being bonded to another member while the elastic member is extended. "Stretch bonded laminate" or SBL refers to a composite material having at least two layers in which one layer is a gatherable layer and the other layer is an elastic layer. The layers are joined together when the elastic layer is in an extended condition so that upon relaxing the layers, the gatherable layer is gathered. Such a multilayer composite elastic material may be stretched to the extent that the nonelastic material gathered between the bond locations allows the elastic material to elongate. One type of multilayer composite elastic material is disclosed, for example, by U.S. Pat. No. 4,720,415 to Vander Wielen et al., which is hereby incorporated by reference in its entirety, and in which multiple layers of the same polymer produced from multiple banks of extruders are used. Other composite elastic materials are disclosed in U.S. Pat. Nos. 4,789,699 to Kieffer et al., 4,781,966 to Taylor and 4,657,802 and 4,652,487 to Morman and 4,655,760 and 4,692,371 to Morman et al.

Conventionally, "neck bonded" refers to an elastic member being bonded to a non-elastic member while the non-elastic member is extended or necked. "Neck bonded laminate" or NBL refers to a composite material having at least two layers in which one layer is a necked, non-elastic layer and the other layer is an elastic layer. The layers are joined together when the non-elastic layer is in an extended condition. Examples of neck-bonded laminates are such as those described in U.S. Pat. Nos. 5,226,992, 4,981,747, 4,965,122 and 5,336,545 to Morman.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. Nos. 4,340,563 to Appel et al., and 3,692,618 to Dorschner et al., 3,802,817 to Matsuki et al., 3,338,992 and 3,341,394 to Kinney, 3,502,763 to Hartman, 3,502,538 to Levy, and 3,542,615 to Dobo et al. Spunbond fibers are generally not tacky when they are deposited onto a collecting surface. Spunbond fibers are microfibers which are generally continuous and have average diameters (from a sample size of at least 10) larger than 7 microns, more particularly, between about 10 and 30 microns.

As used herein the term "meltblown fibers" means fibers formed by extruding a molten thermoplastic material through a plurality of fine, usually circular, die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buntin. Meltblown fibers are microfibers which may be continuous or discontinuous, are generally smaller than 10 microns in average diameter, and are generally, though not necessarily, tacky when deposited onto a collecting surface.

Spunbond and meltblown fabrics may be combined into "SMS laminates" wherein some of the layers are spunbond and some meltblown such as a spunbond/meltblown/spunbond (SMS) laminate as disclosed in U.S. Pat. Nos. 4,041,203 to Brock et al., 5,169,706 to Collier, et al, and 4,374,888 to Bornslaeger. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic, syndiotactic and random symmetries.

As used herein the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. Nos. 5,108,820 to Kaneko et al., 5,336,552 to Strack et al., and 5,382,400 to Pike et al. For two component fibers, the polymers may be present in ratios of 75/25, 50/50, 25/75 or any other desired ratios.

As used herein the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein, the term "machine direction" or MD means the length of a fabric in the direction in which it is produced. The term "cross machine direction" or CD means the width of fabric, i.e. a direction generally perpendicular to the MD.

As used herein the term "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc. These additives, e.g. titanium dioxide for coloration, are generally present in an amount less than 5 weight percent and more typically about 2 weight percent.

As used herein, through air bonding or "TAB" means a process of bonding a nonwoven bicomponent fiber web in which air which is sufficiently hot to melt one of the polymers of which the fibers of the web are made is forced through the web. The air velocity is between 100 and 500 feet per minute and the dwell time may be as long as 6 seconds. The melting and resolidification of the polymer provides the bonding. Through air bonding has restricted variability and is generally regarded a second step bonding process. Since TAB requires the melting of at least one component to accomplish bonding, it is restricted to webs with two components such as bicomponent fiber webs.

As used herein, the term "stitchbonded" means, for example, the stitching of a material in accordance with U.S. Pat. Nos. 4,891,957 to Strack et al, or 4,631,933 to Carey, Jr.

As used herein, "ultrasonic bonding" means a process performed, for example, by passing the fabric between a sonic horn and anvil roll as illustrated in U.S. Pat. No. 4,374,888 to Bornslaeger.

As used herein "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds and a wire weave pattern looking as the name suggests, e.g. like a window screen. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, the term "personal care product" means diapers, training pants, absorbent underpants, adult incontinence products, and feminine hygiene products.

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets, and the like.

TEST METHODS

Hydrohead: A measure of the liquid barrier properties of a fabric is the hydrohead test. The hydrohead test determines the pressure of water (in millibars) which the fabric will resist before a predetermined amount of liquid passes through. A fabric with a higher hydrohead reading indicates it has a greater barrier to liquid penetration than a fabric with a lower hydrohead. The hydrohead test is performed according to Federal Test Standard No. 191A, Method 5514.

DETAILED DESCRIPTION OF THE INVENTION

Thermoplastic polymers are useful in the production of films, fibers and webs for use in a variety of products such as personal care products, infection control products, garments and protective covers. In many applications it is desirable that the film, fiber or web be elastic so that the products made with the film, fiber or web can conform to an object or so that it may stretch somewhat without failing.

Particular application of elastic materials is in the field of personal care products like feminine hygiene products, incontinence products, diapers and training pants and in the field of infection control products. More particularly, within the realm of personal care products, there is a need for a highly conforming fluid barrier material which will function as a barrier while also conforming to the body. Specific examples of such a use are as containment flaps for diapers and as outercover materials. It is also desired that such a fabric be usable as a liner for personal care products where rapid pass-through of liquids is desired. In such uses, treatments to increase the hydrophilicity of the fabric are probably needed.

Diaper containment flaps are currently made from, for example, nonelastic nonwoven materials with strands of LYCRA® elastic material attached to it. This material functions but has a drawback in that it can leave red marks on children's legs since the strands of material are in only a few locations and these strands are very highly stretched. The LYCRA® elastic strand material is based on spunbond fabric.

Another elastic material which may be used in personal care products is a spunbond or meltblown product using a polyurethane elastomer. This material is available from the Kanebo corporation.

Another elastic material is a copolyetherester meltblown material available under the tradename DEMIQUE® from the Kimberly-Clark Corporation of Dallas, Tex. DEMIQUE® elastomeric fabric is made from a polymer known as ARNITEL®, formerly available from Akzo Plastics of Arnhem, Holland and now available from DSM of Sittard, Holland. DEMIQUE® elastomeric fabric has a relatively poor hand in that it feels somewhat rubbery to the touch.

Yet another material used in personal care products is a meltblown fabric made from a block copolymer elastomer available under the tradename KRATON® from the Shell Chemical Co. of Houston, Tex. The elastomeric nonwoven web may be formed from, for example, elastomeric (polystyrene/poly(ethylene-butylene)/polystyrene) block copolymers. KRATON® block copolymers are available in several different formulations, a number of which are identified in U.S. Pat. Nos. 4,663,220 and 5,304,599, hereby incorporated by reference. KRATON® fabric, like DEMIQUE® fabric, has a relatively poor, rubbery hand, which makes it somewhat undesirable for a product which must come in contact with the skin and therefore is used with a facing material on each side.

Traditional elastic meltblown fabrics alone have been found to have inadequate barrier properties to function as a containment flap.

A successful material for use in a personal care product as, for example, a containment flap, must have good barrier properties, breathability and ideally be fully elastic while preferably not being unpleasant (e.g. rubbery) to the touch. A containment flap made from a material having such properties is the subject of this invention.

The barrier properties of a fabric may be measured using the hydrohead test. This test determines the pressure of water (in millibars) which the fabric will resist before a predetermined amount of liquid passes through. A fabric with a higher hydrohead reading indicates it has a greater barrier to liquid penetration than a fabric with a lower hydrohead. The hydrohead value of a material will be influenced by such factors as the size of the fibers, finer fibers producing smaller pores for liquid to pass through, and the hydrophobicity of the fibers. In functioning as a containment flap in a personal care product, for example, the hydrohead value of a material must be sufficiently high to prevent liquid from passing beyond the fabric and leaking. The inventors believe that a material having a hydrohead value of at least 4 millibars is necessary in containment flap applications and which, while not exceedingly high, is sufficient under most circumstances.

The fabric of this invention may be made into a containment flap and attached to a personal care product liner as is conventionally done with current containment flaps. Alternatively, the material of this invention may be made into a unitary liner and containment flap for a personal care product wherein the liner may include an integral containment flap, thereby avoiding the step of bonding a separate flap to a liner. The liner portion of this embodiment can also include treatments to increase hydrophilicity. This advantage is economic in avoiding a manufacturing step and should also improve comfort by avoiding a seam in the product.

It is unnecessary for the material of this invention when used as a containment flap to have any treatments applied to it. Liners for personal care products, however, often are treated in some manner, usually topically, in certain areas to increase particular properties. A liner may be locally treated to increase wettability in certain areas in order to increase the rate at which liquid passes through the liner to the absorbent material below. Such treatment chemicals, e.g. wetting agents, are known in the art and include Triton® X-102. Liner material may also be apertured or perforated in some manner to increase permeability as well. These examples of a liner, containment flap and unitary containment flap and liner, treated and/or apertured, are intended to be within the scope of the invention.

It is preferred that the fabric of this invention be used alone as a single layer fabric. For certain applications, however, it may be desirable to combine this fabric with other fabrics in an NBL, SBL or SMS structure. Such structures are intended to be within the scope of this invention.

Elasticity is a key property in applications such as containment flaps since the fabric will be in contact with the skin and must be able to bend and stretch with the activity of the normal wearer (or even with the activity of a typical two year old), while retaining its other properties without "red marking". A nonelastic fabric stretches without recovery in this service and sags and so is of little or no use in preventing external leakage. A fabric having elastisticity provided by just a few individual strands can result in red marking and so is also less than ideal. A fully elastic fabric can conform to the wearer's body without red marking and gapping or sagging.

The three most critical need areas discussed above (barrier, breathability, elasticity) are satisfied by the fabric of this invention while also providing a comparatively pleasing hand when compared to, for example, Kraton® and Demique® fabrics. The fabric of this invention provides a hydrohead above 4 mbar, is elastic and importantly, may be used as a containment flap without any other layers attached to it for support or other functions.

Elastomeric polymers have been used in the past for such applications and are somewhat limited by their intrinsic properties as mentioned above (e.g. rubbery hand, poor barrier properties). These materials have recently been joined by a new class of polymers which, when made into fabric, has excellent barrier, breathability, elasticity and a pleasing hand. The new class of polymers is referred to as "metallocene" polymers or as produced according to the metallocene process.

The metallocene process generally uses a metallocene catalyst which is activated, i.e. ionized, by a co-catalyst. Metallocene catalysts include bis(n-butylcyclopentadienyl) titanium dichloride, bis(n-butylcyclopentadienyl)zirconium dichloride, bis(cyclopentadienyl)scandium chloride, bis (indenyl)zirconium dichloride, bis(methylcyclopentadienyl) titaniumdichloride, bis(methylcyclopentadienyl) zirconium dichloride, cobaltocene, cyclopentadienyltitanium trichloride, ferrocene, hafnocene dichloride, isopropyl (cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow.

The metallocene process, and particularly the catalysts and catalyst support systems are the subject of a number of patents. U.S. Pat. No. 4,542,199 to Kaminsky et al. describes a procedure wherein methylaluminoxane (MAO) is added to toluene, the metallocene catalyst of the general formula (cyclopentadienyl)2MeRHal wherein Me is a transition metal, Hal is a halogen and R is cyclopentadienyl or a C1 to C6 alkyl radical or a halogen, is added, and ethylene is then added to form polyethylene. U.S. Pat. No. 5,189,192 to LaPointe et al. and assigned to Dow Chemical describes a process for preparing addition polymerization catalysts via metal center oxidation. U.S. Pat. No. 5,352,749 to Exxon Chemical Patents, Inc. describes a method for polymerizing monomers in fluidized beds. U.S. Pat. No. 5,349,100 describes chiral metallocene compounds and preparation thereof by creation of a chiral center by enantioselective hydride transfer.

Co-catalysts are materials such as methylaluminoxane (MAO) which is the most common, other alkylaluminums and boron containing compounds like tris (pentafluorophenyl)boron, lithium tetrakis (pentafluorophenyl)boron, and dimethylanilinium tetrakis (pentafluorophenyl)boron. Research is continuing on other co-catalyst systems or the possibility of minimizing or even eliminating the alkylaluminums because of handling and product contamination issues. The important point is that the metallocene catalyst be activated or ionized to a cationic form for reaction with the monomer(s) to be polymerized.

Polymers produced using metallocene catalysts have the unique advantage of having a very narrow molecular weight range. Polydispersity numbers (Mw/Mn) of below 4 and as even below 2 are possible for metallocene produced polymers. These polymers also have a narrow short chain branching distribution when compared to otherwise similar Ziegler-Natta produced type polymers.

It is also possible using a metallocene catalyst system to control the isotacticity of the polymer quite closely when stereo selective metallocene catalysts are employed. In fact, polymers have been produced having an isotacticity of in excess of 99 percent. It is also possible to produce highly syndiotactic polypropylene using this system.

Controlling the isotacticity of a polymer can also result in the production of a polymer which contains blocks of isotactic and blocks of atactic material alternating over the length of the polymer chain. This construction results in an elastic polymer by virtue of the atactic portion. Such polymer synthesis is discussed in the journal *Science*, vol. 267, (13 Jan. 1995) at p. 191 in an article by K. B. Wagner. Wagner, in discussing the work of Coates and Waymouth, explains that the catalyst oscillates between the stereochemical forms resulting in a polymer chain having running lengths of isotactic sterocenters connected to running lengths of atactic centers. Isotactic dominance is reduced producing elasticity. Geoffrey W. Coates and Robert M. Waymouth, in an article entitled "Oscillating Stereocontrol: A Strategy for the Synthesis of Thermoplastic Elastomeric Polypropylene" at page 217 in the same issue, discuss their work in which they used metallocene bis(2-phenylindenyl) zirconium dichloride in the presence of methylaluminoxane (MAO), and, by varying the pressure and temperature in the reactor, oscillate the polymer form between isotactic and atactic.

Commercial production of metallocene polymers is somewhat limited but growing. Such polymers are available from Exxon Chemical Company of Baytown, Tex. under the trade name ACHIEVE® for polypropylene based polymers and EXACT® for polyethylene based polymers, Dow Chemical Company of Midland, Mich. has polymers commercially available under the name ENGAGE®. These materials are believed to be produced using non-stereo selective metallocene catalysts. Exxon generally refers to their metallocene catalyst technology as "single site" catalysts while Dow refers to theirs as "constrained geometry" catalysts under the name INSITE® to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade. In the practice of the instant invention, elastic polyolefins like polypropylene and polyethylene are preferred, most especially elastic polypropylene.

Regarding metallocene based elastomeric polymers, U.S. Pat. No. 5,204,429 to Kaminsky et al. describes a process which may produce elastic copolymers from cycloolefins and linear olefins using a catalyst which is a sterorigid chiral metallocene transition metal compound and an aluminoxane. The polymerization is carded out in an inert solvent such as an aliphatic or cycloaliphatic hydrocarbon such as toluene. The reaction may also occur in the gas phase using the monomers to be polymerized as the solvent. U.S. Pat. Nos. 5,278,272 and 5,272,236, both to Lai et al., assigned to Dow Chemical and entitled "Elastic Substantially Linear Olefin Polymers" describe polymers having particular elastic properties.

A number of samples of material were tested in order to determine their barrier properties. The materials are described below and the results given in Table 1. Note that only the Examples are considered by the inventors to be within the practice of their invention.

Comparative 1—This fabric is a meltblown DEMIQUE® elastomeric material made from ARNITEL® polymer. This fabric has a basis weight of 35 gsm with fibers having an average diameter of less than 10 microns.

Comparative 2—This fabric is a meltblown elastic polyurethane fabric from the Kanebo corporation. This fabric has a basis weight of 54 gsm with fibers having an average diameter of less than 10 microns.

Comparative 3—This fabric is a meltblown elastic fabric made from a KRATON® polymer. This elastic material is a block copolymer of styrene/ethylene/propylene/styrene (SEPS) having a melt flow rate of 16 grams/10 minutes at 230° C. and 2160 grams according to ASTM test 1238-90b and the particular grade number designation was KRATON® G-2755. This fabric has a basis weight of 34 gsm.

Comparative 4—This fabric is a laminate of spunbond/meltblown/spunbond (SMS) fabric commercially used as a containment flap in diapers marketed by Kimberly-Clark Corporation as Huggies® disposible diapers. This material has a spunbond layer of polypropylene polymer thermally point bonded to a meltblown layer of polypropylene. The spunbond and meltblown layers are present in a basis weight ratio of between about 1:1 and 1:4.

Example 1—The fabric is a meltblown elastic fabric made from a polymer available from the Dow Chemical Co. of Midland, Mich. under the trade name ENGAGE® elastic polymer. This fabric has a basis weight of 1 osy (34 gsm). This material is a polyethylene copolymer having a melt flow index of 30 grams/10 minutes at 190° C. and 2160 grams according to ASTM test 1238-90b. The spinneret hole size was 145 thousands of an inch with a polymer throughput of 0.52 pounds/inch/hour (PIH) at a height of 8 inches (20 cm) above the forming wire. The fibers were spun at a melt temperature of 420° F. (215° C.), with an air gap of 90 thousands of an inch and in a recessed configuration of 125–150 thousands of an inch. The primary air pressure was 0.9 psig and primary air temperature was 567° F. (297° C.).

Example 2—This fabric is a meltblown elastic fabric made from a polyethylene polymer designated EXACT® 4014 by the Exxon Chemical Company of Houston, Tex. This fabric has a basis weight of 1 osy (34 gsm). The spinneret hole size was 145 thousands of an inch with a polymer throughput of 0.56 pounds/inch/hour (PIH) at a height of 9 inches (2:3 cm) above the forming wire. The fibers were spun at a melt temperature of 480° F. (249° C.), with an air gap of 90 thousands of an inch and in a recessed configuration of 125–150 thousands of an inch. The primary air pressure was 0.9 psig and primary air temperature was 510° F. (266° C.).

TABLE 1

| Hydrohead (mbar) | |
| --- | --- |
| Comparative 1* | Not Discernible (N.D.) |
| Comparative 2* | N.D. |
| Comparative 3* | N.D. |
| Comparative 4* | 33.6 |
| Example 1** | 5.2 |
| Example 2* | 7.2 |

*Average of 5 readings
**Average of 3 readings. Two additional readings were N.D.

Note that one piece of fabric of Example 2 was tested and had five N.D. readings, though the inventors believe that this piece of fabric was defective due to manufacturing problems.

The results in Table 1 show that the material of this invention has barrier properties. The fabric is also elastic. In addition, the fabric feels non-rubbery to the touch and in fact has a more cloth-like feel than most other uncovered elastomeric fabrics, i.e., those without facing materials. This is unique since most elastomeric fabrics with this level of bondability and stretch tend to have a rubbery or tacky surface feel. The material of this invention has a soft, comfortable, non-rubbery, textile-like hand and appearance.

It has also been found that the fabric of this invention provides a number of other advantages which are not readily apparent upon a cursory examination. In particular, the material of this invention has been found to have good bondability to polyolefins, and since the barrier and breathability properties are good, the material may be made thinner than competitive materials yet maintain nearly the same properties as the competitive materials resulting in less mass for disposal.

Bondability is quite important for a material such as that used in personal cam products since conversion into a finished product requires that the fabric be bonded in some way to other parts of the item. Many materials, when used in a personal care product, must be adhesively connected to the item. The fabric of this invention, because it is a polyolefin like the olefinic polymeric nonwoven, nonelastic material of which most personal care products are made, may be bonded thermally to the rest of the item. Thermal bonding methods like point bonding and through-air bonding are much simpler, more maintenance-free production methods when compared to stitchbonding or adhesive bonding.

Thinness and lightness of weight are critical attributes for a personal care product since they are in intimate contact with the body. The fabric of this invention may be thinner and lighter than competitive materials like SMS fabrics since it may be comprised of only a meltblown layer. This has additional rewards in that, since less material is used in each personal care product, the cost to the consumer may be lower and the cost of disposal, both in economic and environmental terms, is lower for the fabric of this invention than for the competitive fabrics.

Thus it has been shown that the highly conforming, breathable barrier elastic material of this invention provides a mix of attributes which is different from and superior to that of current competitive materials. The fabric of this invention also has superior bondability to other polymers used in personal care products and may be made thinner and more light weight than the competitives. It is especially significant that this fabric has improved softness and conformability than the competitives since it need only be a single layer.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A personal care product fabric comprising a nonwoven web of fibers having a hydrohead of at least 4 mbar, a basis weight of less than 68 gsm and which is made from an elastic polyolefin.

2. A containment flap comprising the fabric of claim 1.

3. A liner comprising the fabric of claim 1.

4. The fabric of claim 3 wherein said liner is treated for wettability in certain areas.

5. The personal care fabric of claim 1 comprising an integral liner and containment flap.

6. The personal care fabric of claim 1 further comprising at least one additional nonwoven layer bonded to said fabric.

7. The fabric of claim 6 wherein at least one of said layers is stretched while bonded.

8. The fabric of claim 5 wherein said nonwoven web is comprised of spunbond fabric and said flap is stretched and bonded to said spunbond fabric while said spunbond fabric is unstretched.

9. The fabric of claim 5 wherein said nonwoven web is comprised of spunbond fabric and is stretched and bonded to said flap while said flap is unstretched.

10. A liner for a personal care product comprising a nonwoven web layer of fibers of less than 10 microns in average diameter, where said web has a hydrohead of at least 4 mbar, a basis weight of less than 68 gsm, which is made from an elastic polyolefin, and which is treated with a topical wetting agent.

11. The liner of claim 10 wherein said liner is apertured.

12. The liner of claim 10 where said topical wetting agent is applied in certain areas.

* * * * *